US00PP16128P3

(12) United States Plant Patent
Olesen et al.

(10) Patent No.: US PP16,128 P3
(45) Date of Patent: Nov. 29, 2005

(54) ROSE PLANT NAME 'POULTW003'

(50) Latin Name: ***Rosa* hybrid**
Varietal Denomination: POULtw003

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 151 days.

(21) Appl. No.: 10/812,756

(22) Filed: Mar. 29, 2004

(65) Prior Publication Data

US 2005/0216978 P1 Sep. 29, 2005

(51) Int. Cl.[7] ..... A01H 5/00

(52) U.S. Cl. ..... Plt./103

(58) Field of Search ..... Plt./103

*Primary Examiner*—Anne Marie Grunberg
*Assistant Examiner*—Annette H Para

(57) ABSTRACT

A new garden rose plant of the shrub rose class which has abundant, near white flowers and attractive foliage. This new and distinct variety has shown to be uniform and stable in the resulting generations from asexual propagation.

1 Drawing Sheet

Botanical classification: *Rosa hybrid.*
Variety denomination: 'POULtw003'.

SUMMARY OF THE INVENTION

The present invention constitutes a new and distinct variety of garden rose plant which originated from a controlled crossing between the female seed parent 'Meidomonac', described and illustrated in U.S. Plant Pat. No. 5,105 issued Sep. 20, 1983, and the male pollen parent, an un-named seedling. The two parents were crossed during the summer of 1991, and the resulting seeds were planted in a controlled environment in Fredensborg, Denmark. The new variety is named 'POULtw003'.

The new variety may be distinguished from its female seed parent, 'Meidomonac' by the following combination of characteristics:

1. The seed parent has flowers with more petals than flowers of 'POULtw003'.
2. While the seed parent has a flower diameter of about 60 mm; flowers of 'Poultw003' are smaller, approximately 45 mm.
3. 'Poultw003' is lighter in color than the seed parent.

The new variety may be distinguished from its male pollen parent by the following combination of characteristics:

1. While the pollen parent has a general tonality Yellow-Orange Group 15A; the same of 'POULtw003' is Yellow Group 4D with intonations of Yellow-Orange Group 16C.
3. The pollen parent has 14 to 18 petals, while 'POULtw003' has 30 petals.

The objective of the hybridization of this rose variety was to create a new and distinct variety for garden use with unique qualities, such as:

1. Uniform and abundant near white flowers;
2. Vigorous, compact, and even growth when propagated on its own roots;
3. Exceptional disease resistance;

4. Continuous flowering;
5. Low growing habit;
6. Self cleaning flower petals.

This combination of qualities is not present in previously available commercial cultivars of this type, known to the inventors, and distinguish 'POULtw003' from all other varieties of which we are aware.

As part of their rose development program, L. Pernille Olesen and Mogens N. Olesen germinated the seeds from the aforementioned hybridization during winter of 1992 and conducted evaluations on the resulting seedlings in a controlled environment in Fredensborg, Denmark.

'POULtw003' was selected in the spring of 1993 by the inventors as a single plant from the progeny of the aforementioned hybridization.

Asexual reproduction of 'POULtw003' by traditional budding and rooted cuttings was first done by L. Pernille and Mogens N. Olesen in their nursery in Fredensborg, Denmark in July, 1993. This initial and other subsequent asexual propagations conducted in controlled environments have demonstrated that the characteristics of 'POULtw003' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULtw003'. Specifically illustrated in the drawing.

FIG. 1.1; Open flower, and cluster of open flowers stem showing open flower, branching, and the attachment of leaves, buds, and peduncles;

FIG. 1.2; Flower petals, detached;

FIG. 1.3; Sepals, receptacle, pedicel and reproductive flower parts;

FIG. 1.4; Mature leaf;

FIG. 1.5; Juvenile stem and flower bud;

FIG. 1.6; Bare stems.

DETAILED DESCRIPTION OF THE VARIETY

The following is a description of 'POULtw003', as observed in its growth in in a field nursery in Jackson County, Oreg. Observed plants are 3 years of age, and were grown on *Rosa multiflora* understock. Color references are made using The Royal Horticultural Society (London, England) Colour Chart, 1995, except where common terms of color are used.

For a comparison, several physical characteristics of the rose variety 'POULdiram', a rose variety from the same inventors described and illustrated in U.S Plant Pat. No. 12,568 and issued on Apr. 23, 2002, are compared to 'POULtw003' in Chart 1.

CHART 1

| | 'POULtw003' | 'POULdiram' |
|---|---|---|
| Sepals, upper surface. | Yellow-Green Group 145C to Green Group 138A. | Yellow-Green Group 144B. |
| Receptacle color. | Green Group 143C. | Yellow-Green Group 144C. |
| Peduncle length. | 16 to 19 mm average length. | 25 to 40 mm average length. |

FLOWER AND FLOWER BUD

Blooming habit: Continuous.

Flower bud:

*Size.*—Upon opening, 21 mm in length from base of receptacle to end of bud. Bud diameter is 8 mm on average.

*Bud form.*—Pointed ovoid.

*Bud color.*—As sepals unfold, petals are Yellow-White Group 158A. At ¼ opening petals are Yellow-White Group 158B.

*Sepals.*—Upper surface: Color: Yellow-Green Group 145C to Green Group 138A. Surface: Medium pubescence observed. Lower surface: Color: Yellow-Green Group 144A. Anthocyanic pigments the color of Greyed-Purple Group 184A. Texture: Smooth with medium stipitate glands. Sepal shape: Sepal apex is cirrhose. Base is flat at union with receptacle. Sepal margin: Margins have strong medium foliaceous appendages on three of the five sepals. Size: 21 mm long by 6 mm wide.

*Receptacle.*—Surface texture: Smooth. Shape: Urn-shaped. Size: 6 mm (h)×4 mm (w). Color: Green Group 143C. Anthocyanic pigments the color of Greyed-Red Group 181B observed.

*Peduncle.*—Surface: Stipitate glands fragrant and smooth. Length: 16 mm to 19 mm average length. Color: Yellow-Green Group 144C. Anthocyanic pigments the color of Greyed-Orange Group 176A observed. Strength: Somewhat strong.

*Borne.*—In clusters of 19 flower buds per stem.

Flower bloom:

*Fragrance.*—Light and floral.

*Duration.*—The blooms have a duration on the plant of approximately 7 to 10 days. Petals fall cleanly away from plant after flowers have fully matured.

*Size.*—Flower diameter is 45 mm when open. Flower depth is 20 mm on average.

*Form.*—General: Open cup, double flower, with petals that curve out from the center. Side view: Upon opening, upper part: Flat. Upon opening, lower part: Convex. Open flower, upper part: Flat. Open flower, lower part: Convex.

Petalage: 30 petals on average under normal conditions with 10 petaloids.

Color:

Upon opening, petals:

*Outermost petals.*—Outer side: Yellow-White Group 158C to Yellow Group 12D. Inner side: Yellow-White Group 158C to Yellow Group 12D.

*Innermost petals.*—Outer side: Yellow-Orange Group 16D. Inner side: Yellow-Orange Group 16D.

Upon opening, basal petal spots:

*Outermost petals.*—Outer side: Yellow-Orange Group 16B. Inner side: Yellow-Orange Group 16A.

*Innermost petals.*—Outer side: Yellow-Orange Group 16B. Inner side: Yellow-Orange Group 16B.

After opening, petals:

*Outermost petals.*—Outer side: Yellow-White Group 158C. Inner side: Yellow-White Group 158C.

*Innermost petals.*—Outer side: Yellow-White Group 158B. Inner side: Yellow-White Group 158B.

After opening, basal petal spots:

*Outermost petals.*—Outer side: Yellow Group 12B. Inner side: Yellow Group 12B.

*Innermost petals.*—Outer side: Yellow-White Group 158B. Inner side: Yellow-White Group 158B with intonations of Yellow-Orange 16D.

General tonality: On open flower Yellow Group 4D with intonations of Yellow-Orange Group 16C. No change in the general tonality at the end of the $10^{th}$ day. Afterwards, general tonality fades to White Group 155B.

Petals:

*Petal reflex.*—None.

*Margin.*—Entire with a point in the center of the petal margin.

*Shape.*—Apex is rounded. Base shape varies from rounded to acute.

*Size.*—18 mm (l)×17 mm (w).

*Texture.*—Smooth.

*Thickness.*—Thin.

*Arrangement.*—Not Formal.

Petaloids:

*Quantity.*—8 to 12.

*Color.*—Upper Surface: White Group 155B. Lower Surface: White Group 155B.

*Size.*—12 mm (l)×4 mm (w).

*Shape.*—Irregular, elliptical. Apex and base are acute.

Reproductive organs:

*Pollen.*—None observed.

*Anthers.*—Size: 1 mm in length. Color: Yellow-Orange Group 23A. Quantity: 41 (actual count).

*Filaments.*—Color: Yellow Group 9A. Length: 4 mm.

*Pistils.*—Length: 4 mm. Quantity: 27 (actual count).

*Stigmas.*—Level relative to the length of the filaments and the height of the anthers. Color: Yellow-Orange Group 23A.

*Styles.*—Color: Red Group 41A.

*Hips.*—None Observed in the field nursery in Jackson County Oreg.

PLANT

Plant growth: Moderately compact. When grown as a budded field grown plant on *Rosa multiflora* understock, the average height of the plant is 60 to 100 cm. Average spread is 60 to 80 cm.

Stems:

*Color.*—Young wood: Greyed-Orange Group 176A. Older wood: Yellow-Green Group 145A to 144B.

*Surface texture.*—Young wood: Smooth. Older wood: Smooth.

Thorns:

*Incidence.*—1 to 2 thorns per 10 cm of stem.

*Size.*—Average length: 10 mm.

*Color.*—Greyed-Orange Group 173C.

*Shape.*—Deeply concave.

Plant foliage: Normal number of leaflets on normal leaves in middle of the stem: 7 leaflets.

*Compound leaf size.*—80 mm (l)×55 mm (w).

*Color of mature foliage.*—Upper surface is Green Group 137A. Lower surface is Yellow-Green Group 147C.

*Color of juvenile foliage.*—Upper surface is Yellow-Green Group 144A. Lower surface is Yellow-Green Group 144B.

Plant leaves and leaflets:

*Stipules.*—Size: 15 mm in length. Shape: Linear, slightly broad based with outward extending apecies. Margins: Finely serrated with few stipitate glands. Color: Yellow-Green Group 144B.

*Petiole.*—Length: 20 mm. Color: Yellow-Green Group 144C. Anthocyanin: None. Underneath: Few stipitate glands and thorns observed.

*Rachis.*—Length: 35 mm. Color: Yellow-Green Group 144C. Anthocyanin: None. Underneath: Few stipitate glands and thorns observed.

*Leaflet.*—Edge: Serrated. Size: 20 to 30 mm (l)×15 to 21 mm (w). Shape: Generally ovate. Apes is slightly cuspidate. Base is rounded. Texture: Smooth. Thickness: Thick. Arrangement: Odd pinnate. Venation: Reticulate. Glossiness: Glossy.

Disease resistance: Above average resistance to mildew, rust, black spot, and *Botrytis* under normal growing conditions in Jackson County, Oreg.

Cold hardiness: The variety 'POULtw003' has been found to be cold tolerant to USDA Cold Hardiness Zone 6.

It is claimed:

1. A new and distinct variety of rose plant of the shrub rose class named 'POULtw003', as illustrated and described due to its abundant near white flowers, disease resistance, and extended period of bloom.

* * * * *

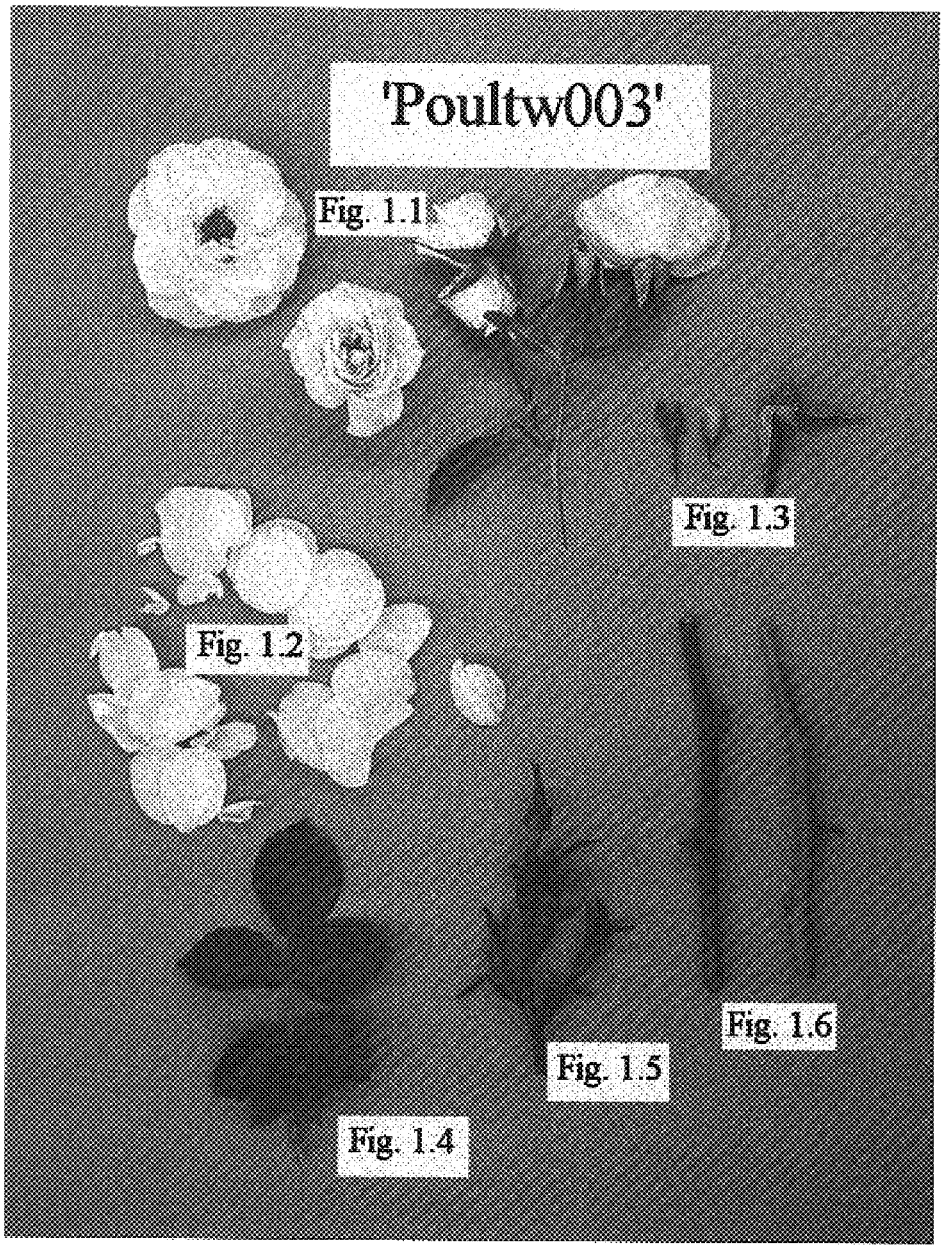
'Poultw003'
Fig. 1.1
Fig. 1.2
Fig. 1.3
Fig. 1.4
Fig. 1.5
Fig. 1.6